(12) United States Patent
Hoffman

(10) Patent No.: US 9,808,248 B2
(45) Date of Patent: Nov. 7, 2017

(54) INSTALLATION FEATURES FOR SURGICAL INSTRUMENT END EFFECTOR CARTRIDGE

(71) Applicant: Ethicon Endo-Surgery, Inc., Cincinnati, OH (US)

(72) Inventor: Douglas B. Hoffman, Harrison, OH (US)

(73) Assignee: Ethicon LLC, Guaynabo, PR (US)

( * ) Notice: Subject to any disclaimer, the term of this patent is extended or adjusted under 35 U.S.C. 154(b) by 622 days.

(21) Appl. No.: 13/780,417

(22) Filed: Feb. 28, 2013

(65) Prior Publication Data

US 2014/0239044 A1   Aug. 28, 2014

(51) Int. Cl.

| A61B 17/068 | (2006.01) |
| A61B 17/072 | (2006.01) |
| A61B 17/00 | (2006.01) |
| A61B 17/29 | (2006.01) |

(52) U.S. Cl.
CPC ........... *A61B 17/07207* (2013.01); *A61B 2017/00398* (2013.01); *A61B 2017/00477* (2013.01); *A61B 2017/07271* (2013.01); *A61B 2017/2927* (2013.01)

(58) Field of Classification Search
CPC .... A61B 17/07207; A61B 2017/00398; A61B 2017/2927; A61B 2017/07271; A61B 2017/00477; A61B 2017/07278; A61B 19/0262
USPC ......... 227/175.1, 175.2, 175.3, 175.4, 176.1, 227/177.1, 178.1, 179.1, 180.1, 181.1, 227/182.1
See application file for complete search history.

(56) References Cited

U.S. PATENT DOCUMENTS

| 4,805,823 A | 2/1989 | Rothfuss |
| 5,275,323 A | 1/1994 | Schulze et al. |
| 5,415,334 A | 5/1995 | Williamson, IV et al. |
| 5,465,895 A | 11/1995 | Knodel et al. |
| 5,562,241 A | 10/1996 | Knodel et al. |
| 5,597,107 A | 1/1997 | Knodel et al. |

(Continued)

FOREIGN PATENT DOCUMENTS

EP   2248475 A1   11/2010

OTHER PUBLICATIONS

Extended European Search Report dated Sep. 10, 2014 for Application No. 14157363.4, 7 pages.

(Continued)

*Primary Examiner* — Thanh Truong
*Assistant Examiner* — Thomas Wittenschlaeger
(74) *Attorney, Agent, or Firm* — Frost Brown Todd LLC

(57) ABSTRACT

A surgical instrument comprises a body, a shaft, and an end effector. The end effector has a staple cartridge, a lower jaw, an anvil, and a firing beam. The staple cartridge comprises a cartridge body and a lower cartridge tray. One or both of the cartridge body or the lower cartridge tray comprises at least one notch. The lower jaw is configured to be coupled with the cartridge body and comprises protrusions. The protrusions of the lower jaw align with the notches of the cartridge body and/or lower cartridge tray when the lower jaw and staple cartridge are coupled. The body comprises a handle portion and a series of actuators capable of closing the anvil on the staple cartridge and driving the firing beam to vertically drive a plurality of staples.

20 Claims, 19 Drawing Sheets

(56) References Cited

U.S. PATENT DOCUMENTS

| | | | |
|---|---|---|---|
| 5,632,432 A | 5/1997 | Schulze et al. | |
| 5,662,258 A | 9/1997 | Knodel et al. | |
| 5,662,667 A | 9/1997 | Knodel | |
| 5,669,544 A | 9/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,044,352 B2 | 5/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,500,979 B2 * | 3/2009 | Hueil | A61B 17/07207 227/175.1 |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,479,969 B2 | 7/2013 | Shelton, IV et al. | |
| 8,573,461 B2 | 11/2013 | Shelton, IV et al. | |
| 8,573,465 B2 | 11/2013 | Shelton, IV et al. | |
| 8,602,288 B2 | 12/2013 | Shelton, IV et al. | |
| 8,616,431 B2 | 12/2013 | Timm et al. | |
| 8,800,841 B2 | 8/2014 | Ellerhorst et al. | |
| 2007/0010838 A1 | 1/2007 | Shelton, IV et al. | |
| 2007/0084897 A1 | 4/2007 | Shelton, IV et al. | |
| 2008/0083809 A1 * | 4/2008 | Scirica | 227/175.1 |
| 2009/0200355 A1 * | 8/2009 | Baxter, III | A61B 17/07207 227/176.1 |
| 2010/0065605 A1 * | 3/2010 | Shelton, VI | A61B 17/07207 227/176.1 |
| 2010/0282816 A1 * | 11/2010 | Scirica | A61B 17/07207 227/176.1 |
| 2010/0320252 A1 * | 12/2010 | Viola | A61B 17/07207 227/176.1 |
| 2011/0226837 A1 * | 9/2011 | Baxter, III | A61B 17/0644 227/175.1 |
| 2011/0290853 A1 * | 12/2011 | Shelton, IV | A61B 17/07207 227/177.1 |
| 2012/0138660 A1 | 6/2012 | Shelton, IV et al. | |
| 2012/0199630 A1 | 8/2012 | Shelton, IV et al. | |
| 2012/0199632 A1 | 8/2012 | Spivey et al. | |
| 2012/0203247 A1 | 8/2012 | Shelton, IV et al. | |
| 2012/0253298 A1 | 10/2012 | Henderson et al. | |
| 2013/0012957 A1 | 1/2013 | Shelton, IV et al. | |

OTHER PUBLICATIONS

International Search Report and Written Opinion dated May 23, 2014 for Application No. PCT/US2014/017334, 9 pages.
U.S. Appl. No. 13/780,067, filed Feb. 28, 2013.
U.S. Appl. No. 13/780,082, filed Feb. 28, 2013.
U.S. Appl. No. 13/780,106, filed Feb. 28, 2013.
U.S. Appl. No. 13/780,120, filed Feb. 28, 2013.
U.S. Appl. No. 13/780,379, filed Feb. 28, 2013.
U.S. Appl. No. 13/780,402, filed Feb. 28, 2013.

* cited by examiner

INSTALLATION FEATURES FOR SURGICAL INSTRUMENT END EFFECTOR CARTRIDGE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartidge with Adhesive for Use with a Stapling Device," issued May 25, 2010; U.S. Pub. No. 2010/0264193, entitled "Surgical Stapling Instrument with An Articulatable End Effector," published Oct. 21, 2010 and issued as U.S Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012 and issued as U.S. Pat. No. 8,453,914 on Jun. 4, 2013. The disclosure of each of the above-cited U.S. Patents and U.S. Patent Publications is incoporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
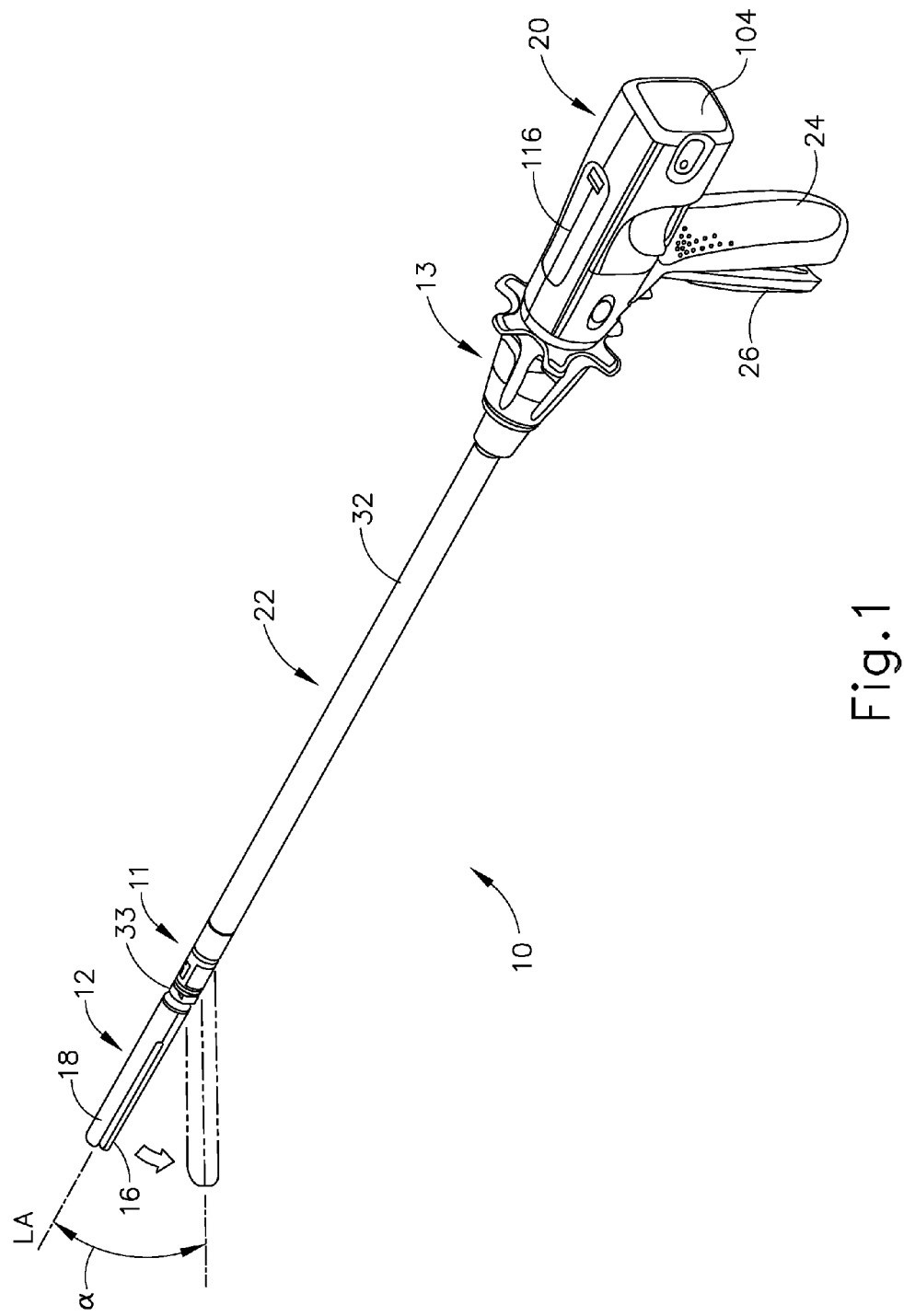
FIG. 1 depicts a perspective view of an exemplary articulating surgical stapling instrument.
Figure 2:
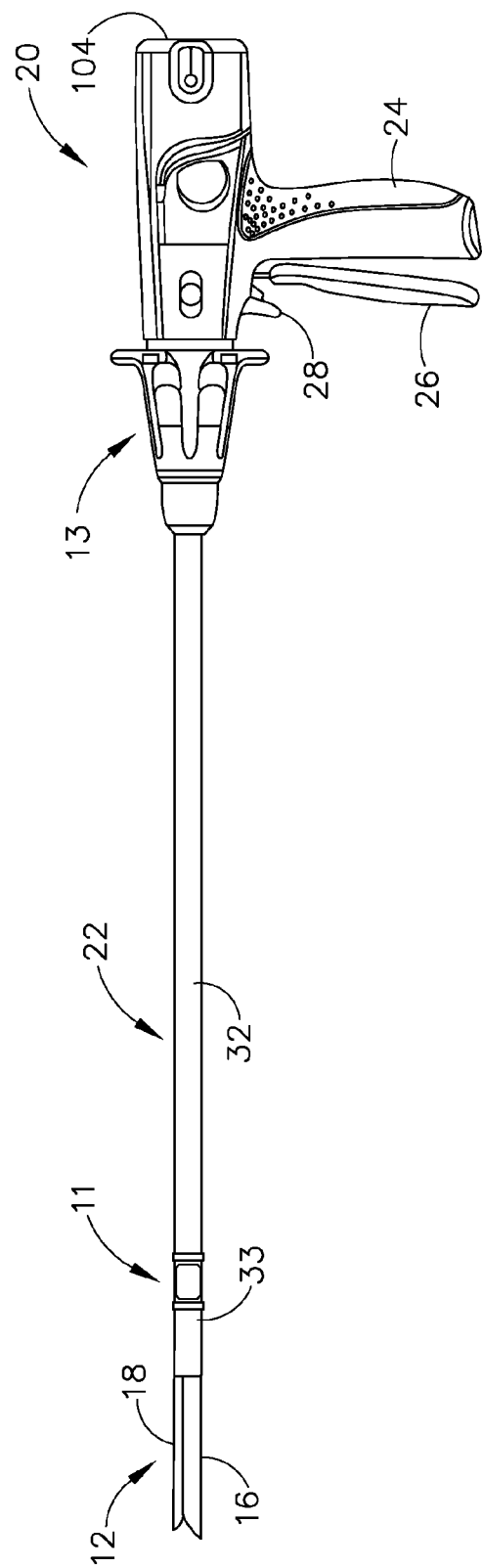
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. patent application Ser. No. 13/780,402, entitled "Surgical Instrument with Multi-Diameter Shaft," filed on Feb. 28, 2013 and published as U.S. Pat. Pub. No. 2014-0239038 on Aug. 28, 2014, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle ($\alpha$). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. patent application Ser. No. 13/780,067, entitled "Surgical Instrument End Effector Articulation Drive with Pinion and Opposing Racks," filed on Feb. 28, 2013 and published as U.S. Pat. Pub. No. 2014-0243801 on Aug. 28, 2014, now U.S. Pat. No. 9,186,142, issued on Nov. 17, 2015, the disclosure of which is incorporated by reference herein. Articulation joint (11) may also be constructed and operable in accordance with at least some of the teachings of U.S. patent application Ser. No. 13/780,402, entitled "Surgical Instrument With Multi-Diameter Shaft," filed on Feb. 28, 2013 and published as U.S. Pat. Pub. No. 2014-0239038 on Aug. 28, 2014, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). Various exemplary components, features, and operabilities that may be incorporated into lower jaw (16) are described in greater detail below. Anvil (18) may be constructed in accordance with at least some of the teachings of U.S. patent application Ser. No. 13/780,106, entitled "Integrated Tissue Positioning and Jaw Alignment Features for Surgical Stapler," filed on Feb. 28, 2013 and published as U.S. Pat. Pub. No. 2014-0239042 on Aug. 28, 2014, now U.S. Pat. No. 9,517,065, issued on Dec. 13, 2016, the disclosure of which is incorporated by reference herein; at least some of the teachings of U.S. patent application Ser. No. 13/780,120, entitled "Jaw Closure Feature for End Effector of Surgical Instrument," filed on Feb. 28, 2013 and published as U.S. Pat. Pub. No. 2014-0239036 on Aug. 28, 2014, the disclosure of which is incorporated by reference herein; and/or at least some of the teachings of U.S. patent application Ser. No. 13/780,379, entitled "Staple Forming Features for Surgical Stapling Instrument," filed on Feb. 28, 2013 and published as U.S. Pat. Pub. No. 2014-0239037 on Aug. 28, 2014, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. patent application Ser. No. 13/780,082, entitled "Lockout Feature for Movable Cutting Member of Surgical Instrument," filed on Feb. 28, 2013 and published as U.S. Pat. Pub. No. 2014-0239041 on Aug. 28, 2014, now U.S. Pat. No. 9,717, 497, issued on Aug. 1, 2017, the disclosure of which is incorporated by reference herein. Other suitable forms that firing beam (14) may take will be apparent to those of ordinary skill in the art in view of the teachings herein.

Figure 3:
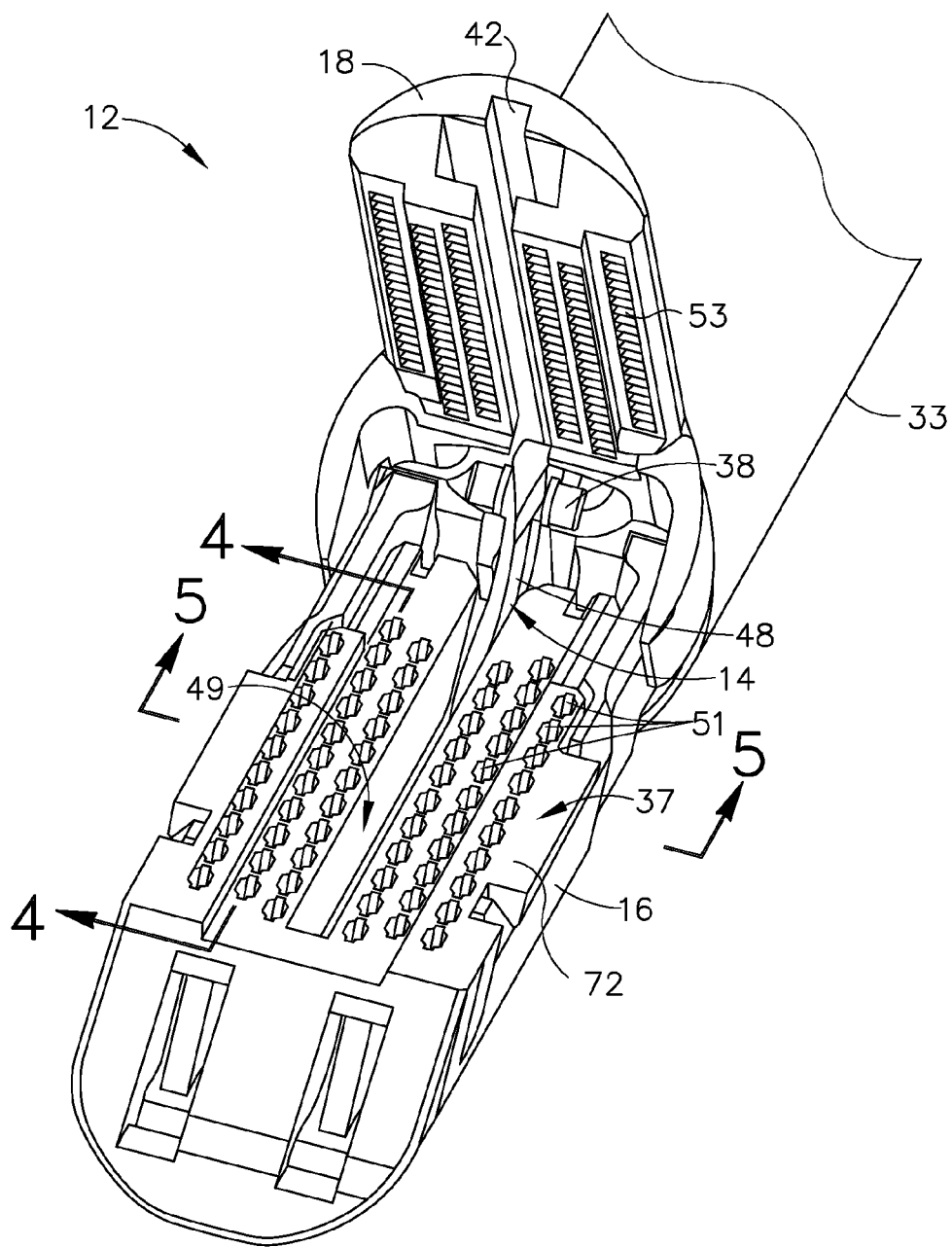
FIG. 3 depicts a perspective view of an opened end effector of the instrument of FIG. 1.
Figure 4A:
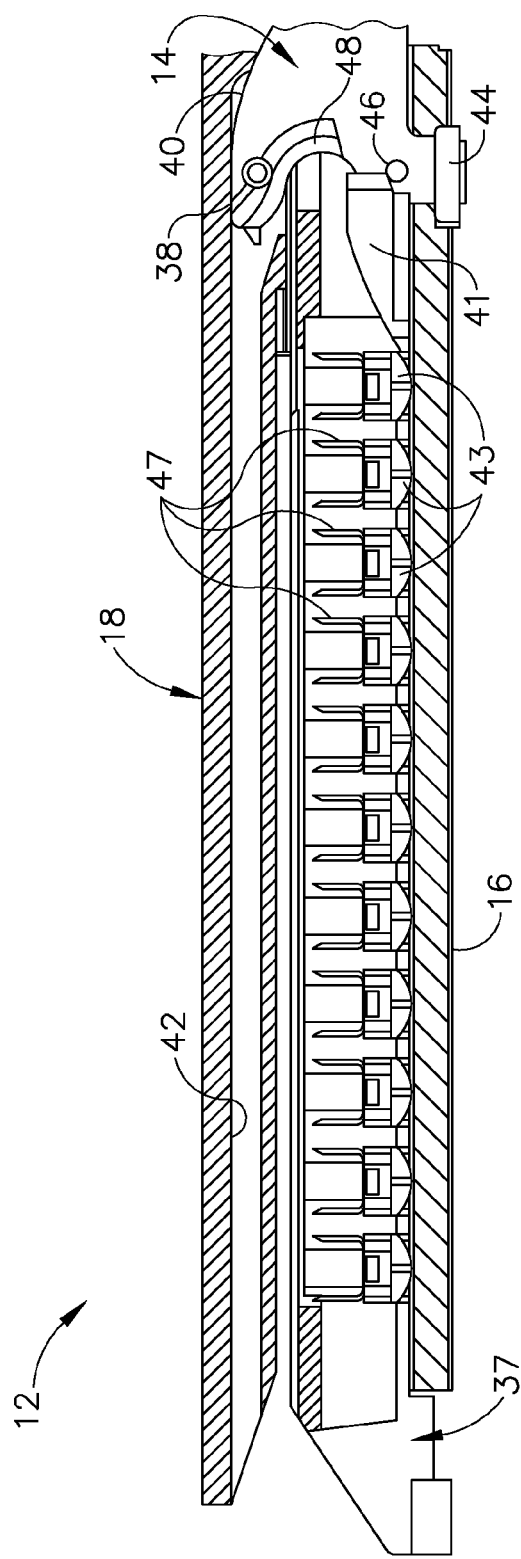
FIG. 4A depicts a side cross-sectional view of the end effector of FIG. 3, taken along line 4-4 of FIG. 3, with a firing beam in a proximal position.
Figure 4B:
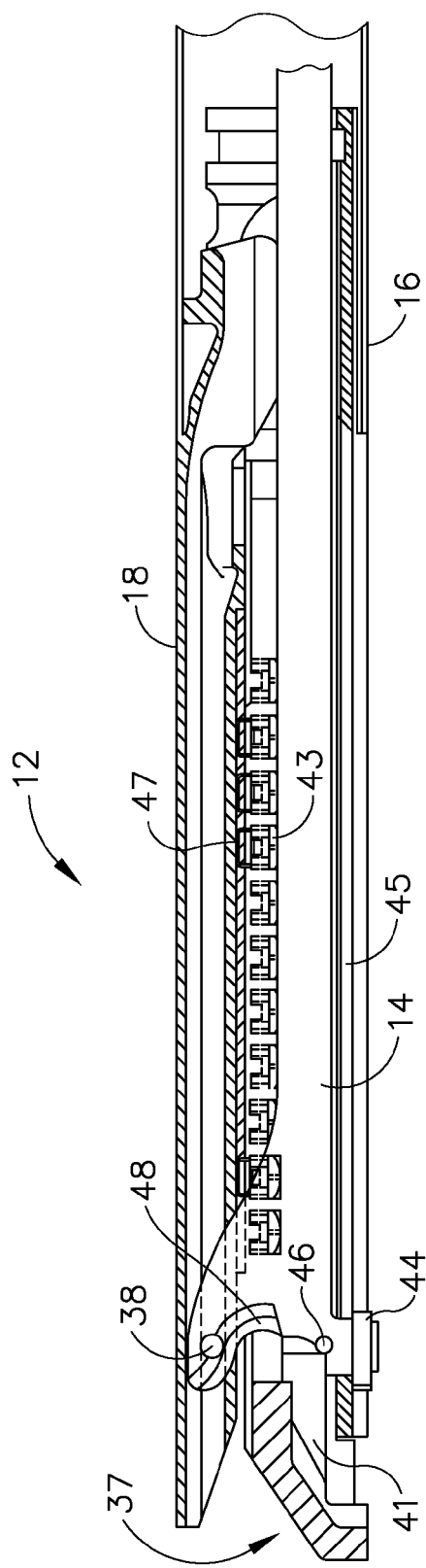
FIG. 4B depicts a side cross-sectional view of the end effector of FIG. 3, taken along line 4-4 of FIG. 3, with the firing beam in a distal position.
Figure 5:
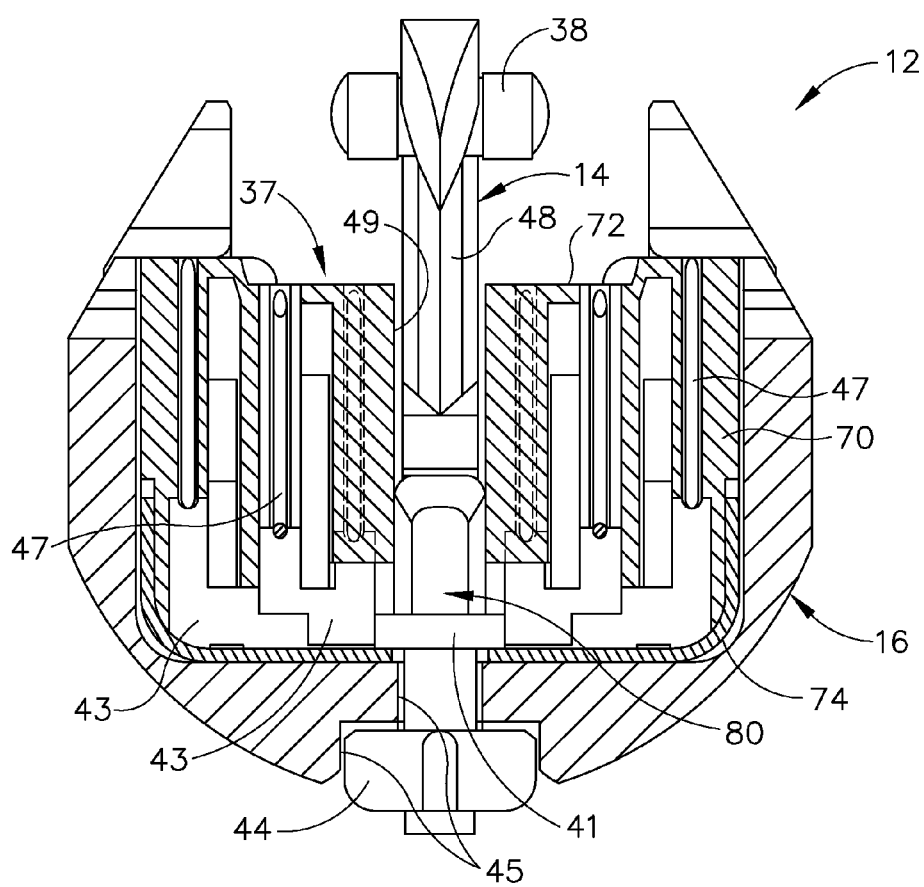
FIG. 5 depicts an end cross-sectional view of the end effector of FIG. 3, taken along line 5-5 of FIG. 3.
Figure 6:
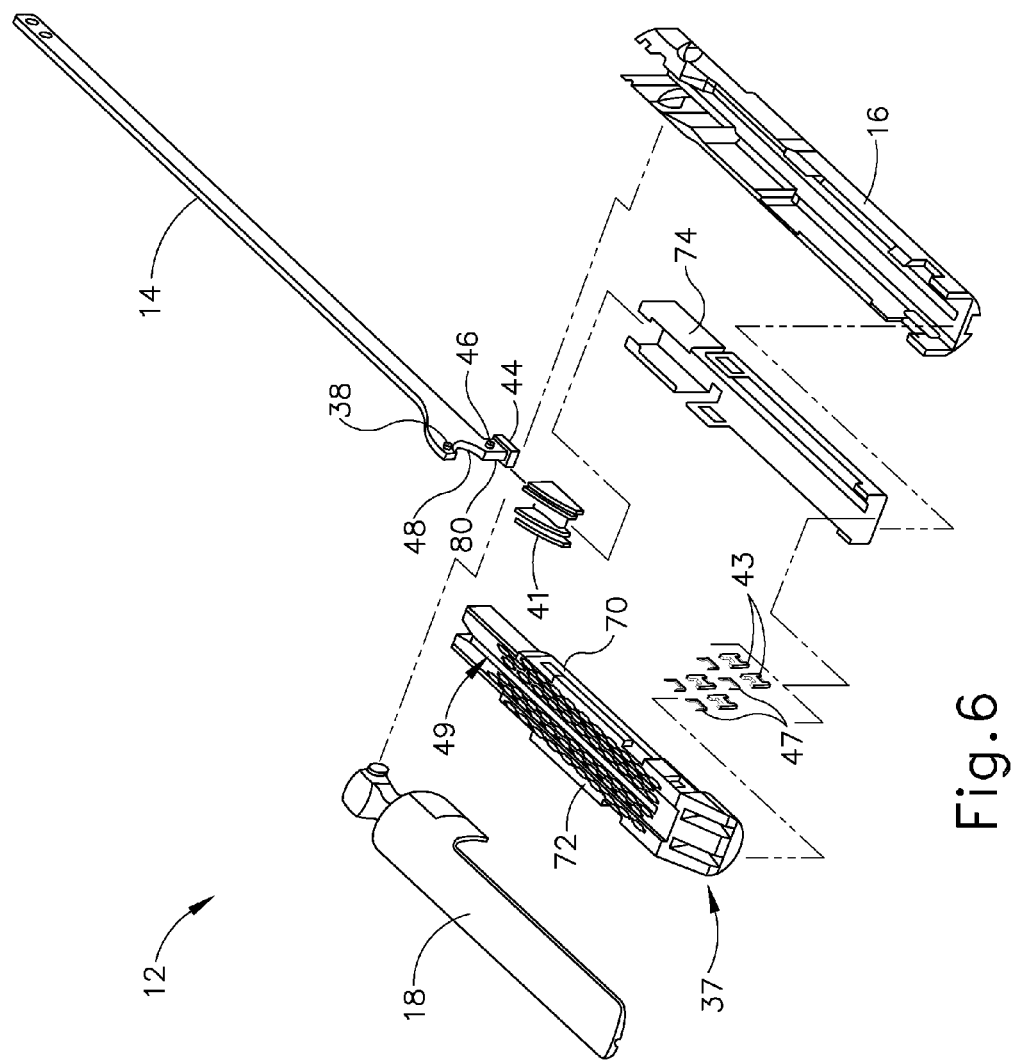
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. patent application Ser. No. 13/780,106, entitled "Integrated Tissue Positioning and Jaw Alignment Features for Surgical Stapler," filed on Feb. 28, 2013 and published as U.S. Pat. Pub. No. 2014-0239042 on Aug. 28, 2014, now U.S. Pat. No. 9,517,065, issued on Dec. 13, 2016, the disclosure of which is incorporated by reference herein. In addition or in the alternative, staple cartridge (37) may be constructed and operable in accordance with at least some of the teachings provided below. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
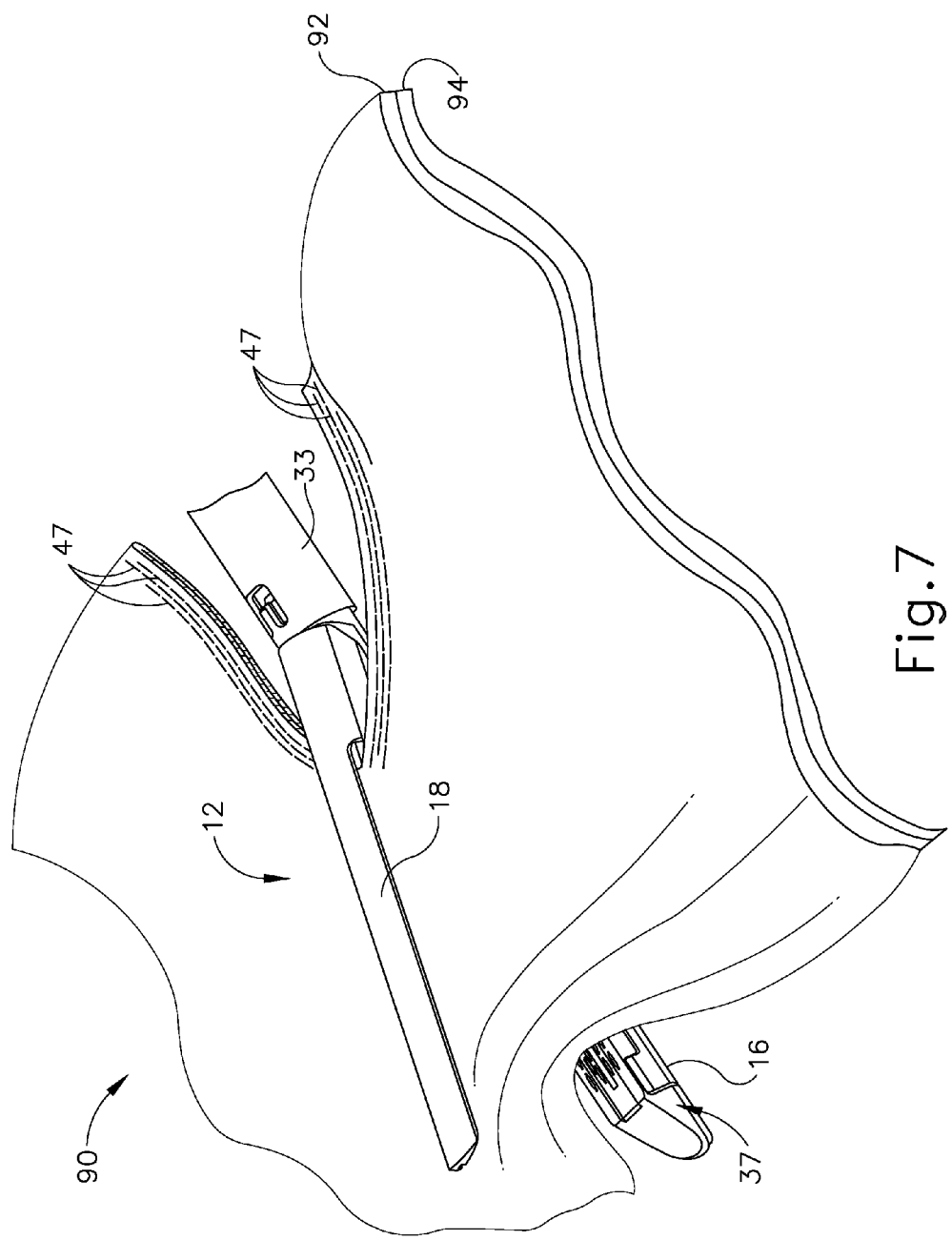
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; U.S. Pub. No. 2010/0264193 (now U.S. Pat. No. 8,408,439) and/or U.S. Pub. No. 2012/0239012 (now U.S. Pat. No. 8,453,914). As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
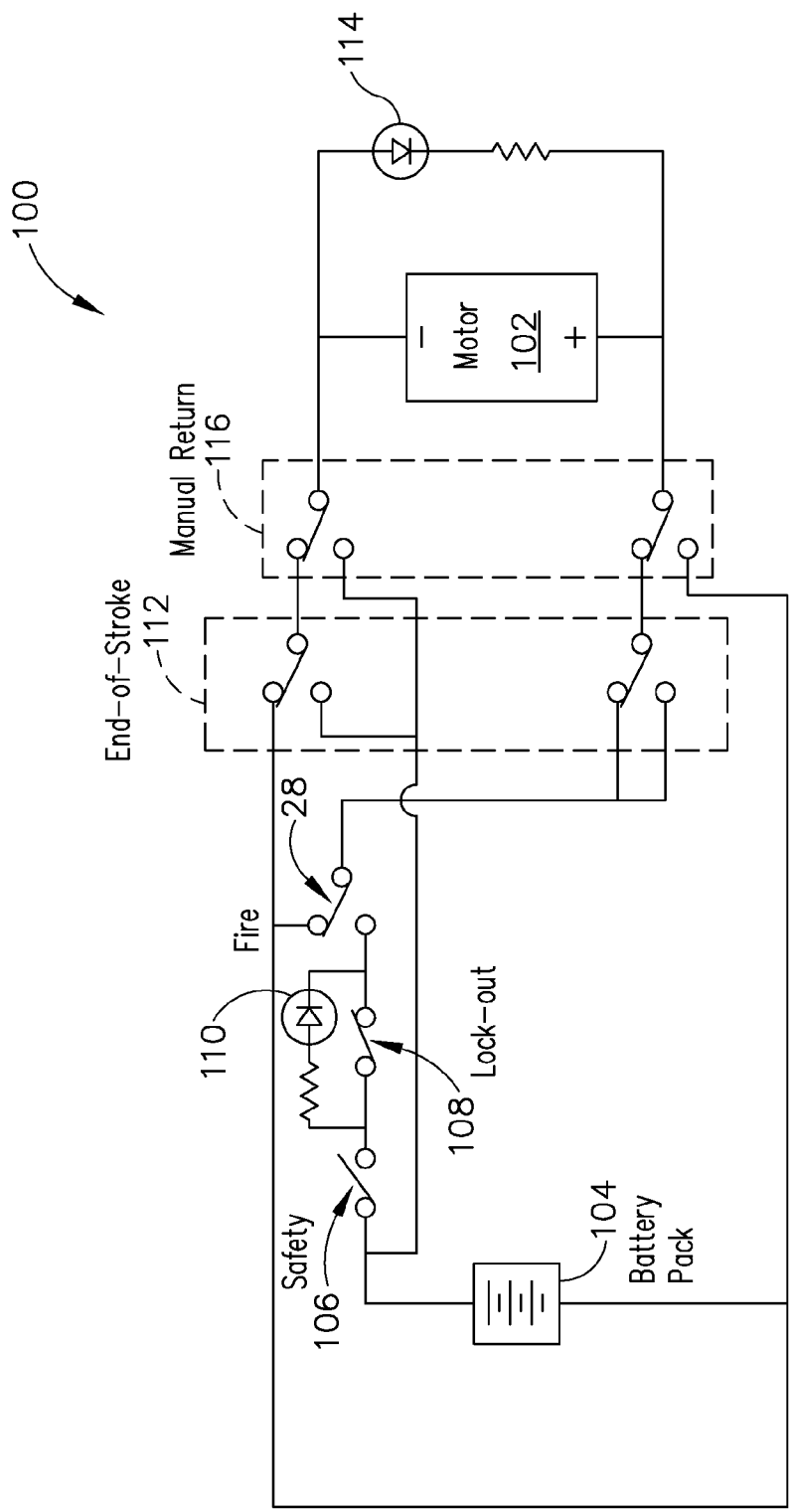
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
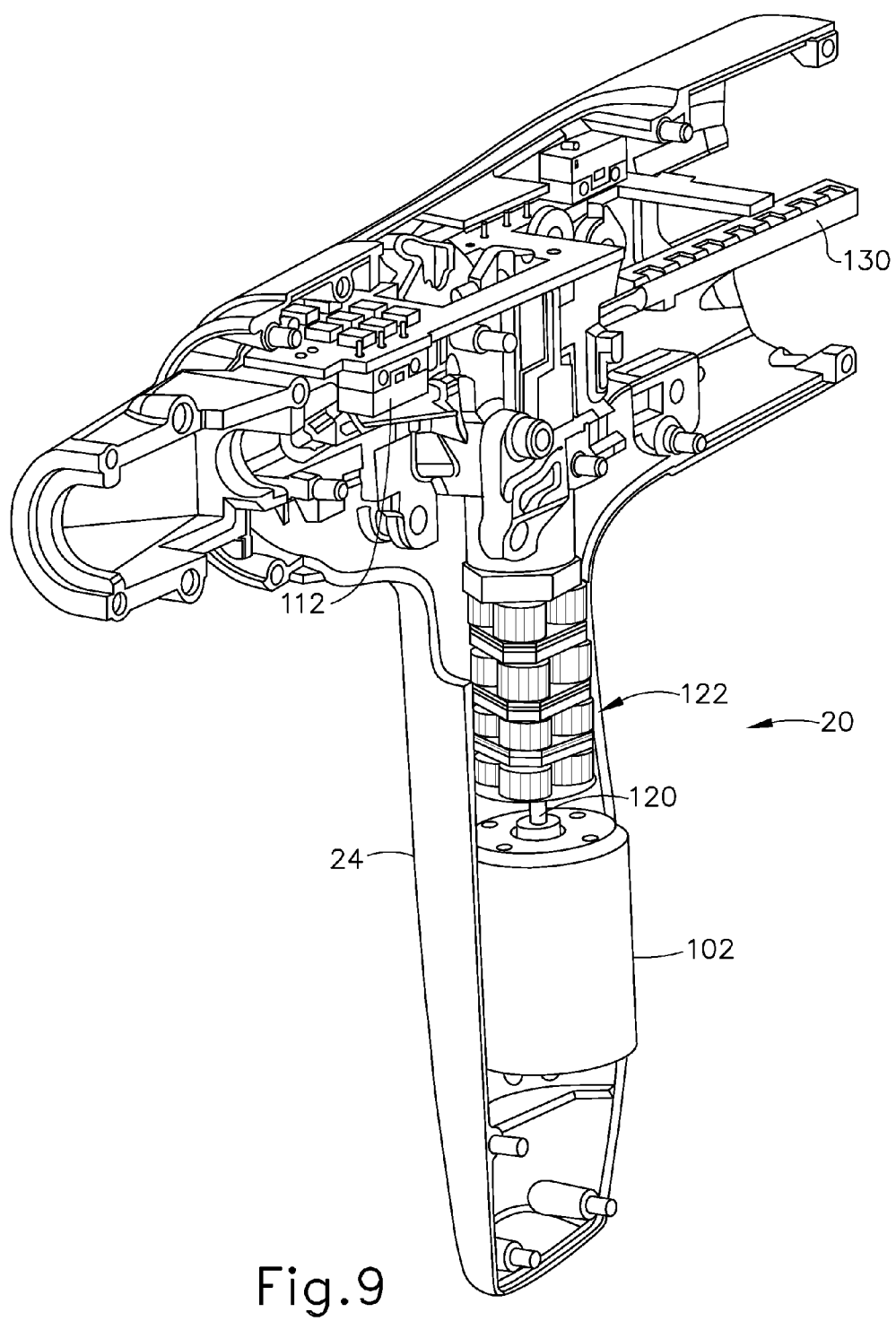
FIG. 9 depicts a perspective view of the handle assembly of the instrument of FIG. 1, with a housing half removed.
Figure 10:
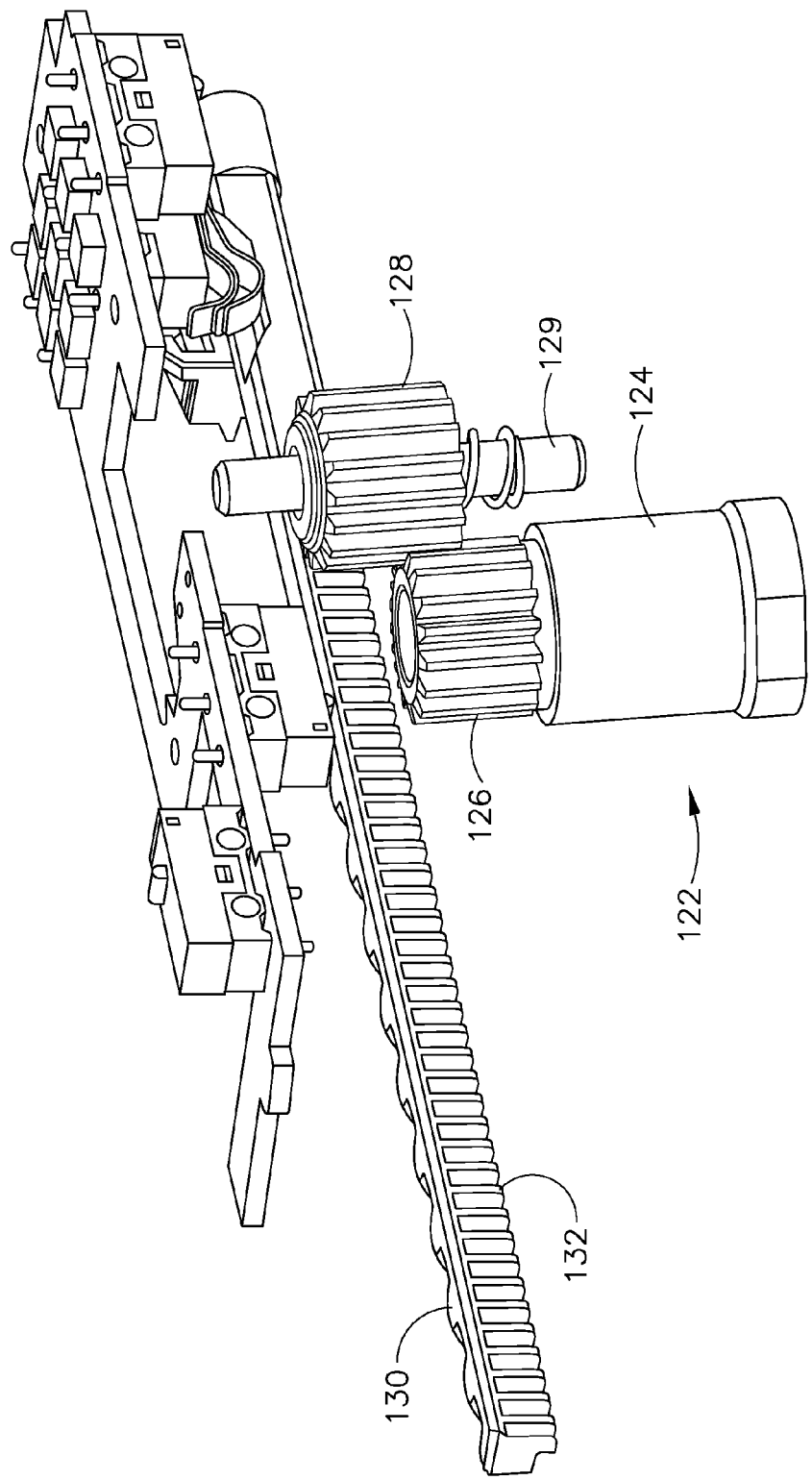
FIG. 10 depicts a perspective view of drive assembly components from the handle assembly of FIG. 9.
Figure 11:
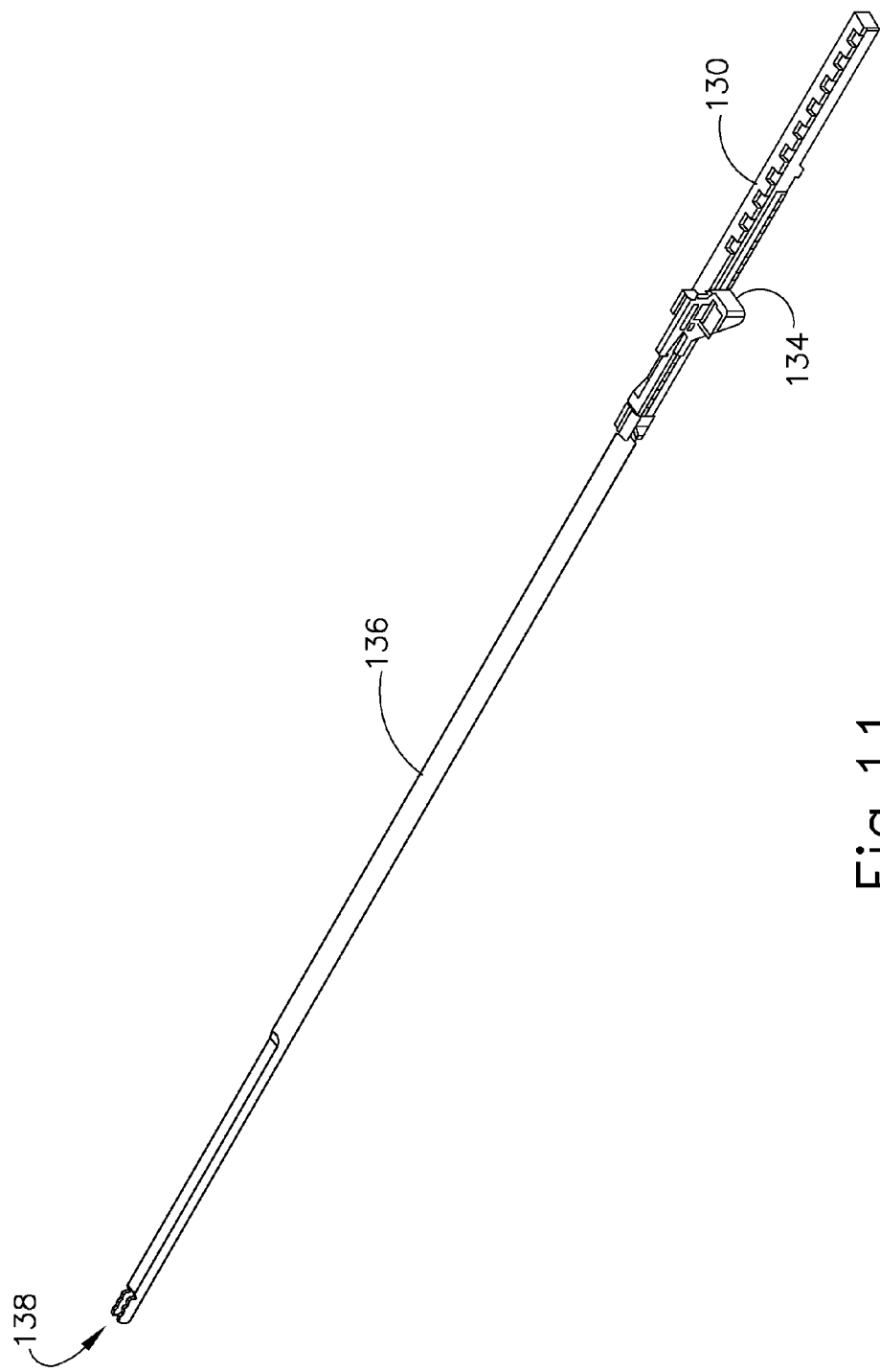
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14) within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012 (now U.S. Pat. No. 8,453,914), the disclosure of which is incorporated by reference herein; and/or in accordance with at least some of the teachings of U.S. Pub. No. 2012/0239012 (now U.S. Pat. No. 8,453,914), the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary Alternative Staple Cartridge and Lower Jaw of End Effector

Figure 12:
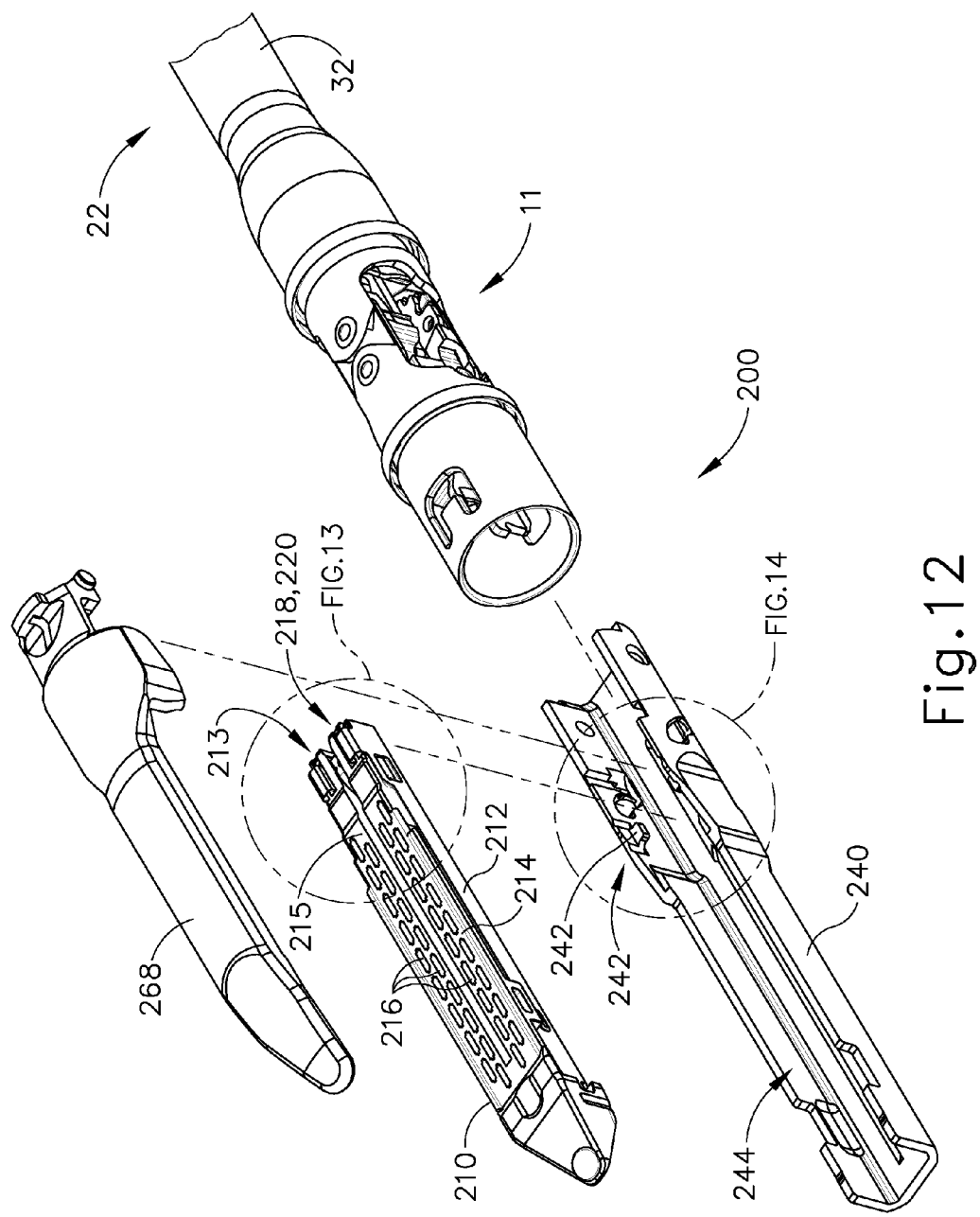
FIG. 12 depicts an exploded perspective view of an exemplary alternative end effector that may be used with the instrument of FIG. 1.

As an alternative to end effector (12) of instrument (10) as discussed above, an exemplary end effector (200) may be used with instrument (10) instead. As shown in FIG. 12, end effector (200) comprises an anvil (268), a lower jaw (240), and a staple cartridge (210) in place of anvil (18), lower jaw (16), and a staple cartridge (37) discussed above.

Anvil (268) comprises a series of staple forming pockets (not shown) and is configured and operable substantially similar to anvil (18) discussed above.

Figure 13:
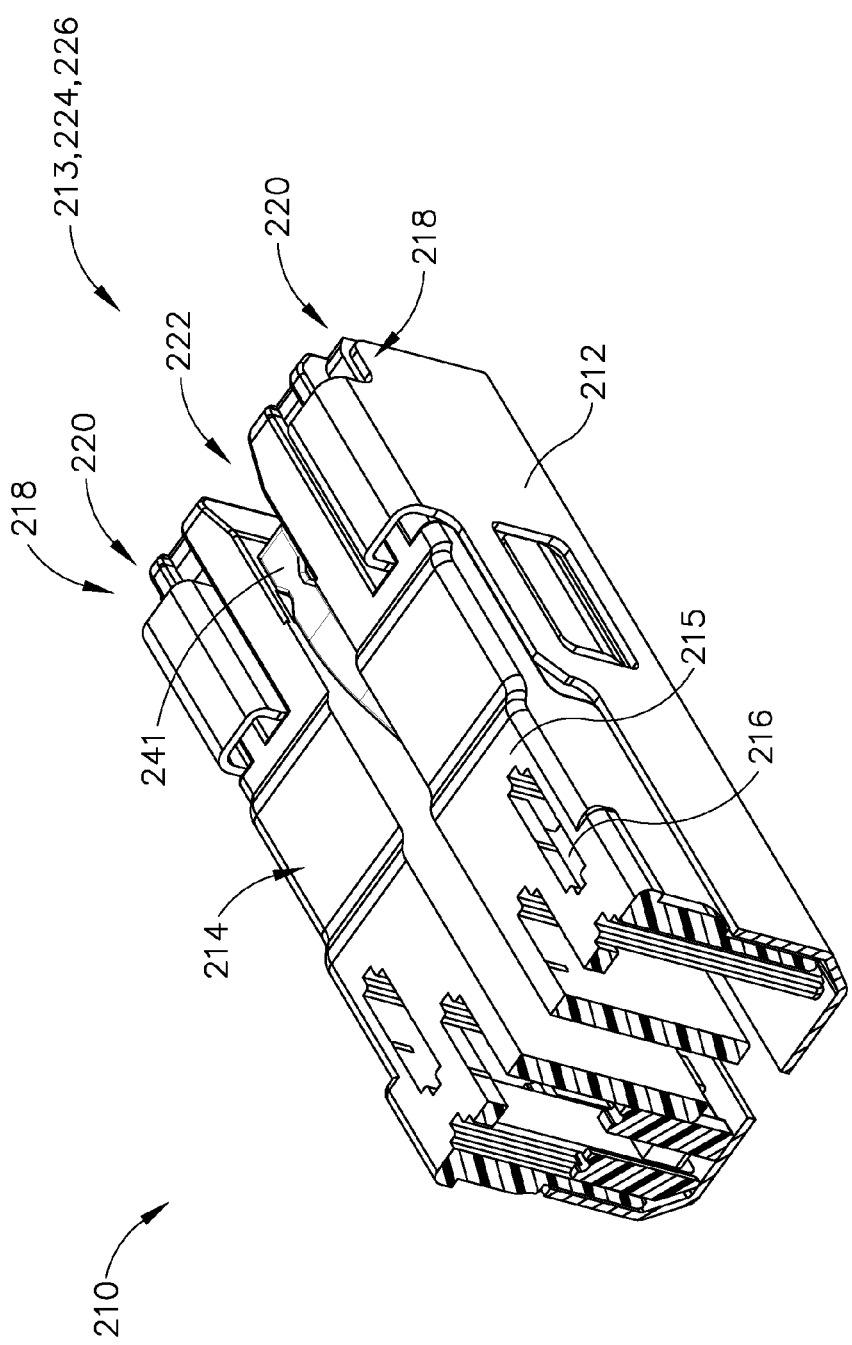
FIG. 13 depicts a detailed perspective view of the proximal portion of an exemplary staple cartridge of the end effector of FIG. 12.

As best seen in FIG. 13, staple cartridge (210) comprises a cartridge body (214), which presents an upper deck (215), and is received within a channel (not shown) of and coupled to a lower cartridge tray (212). Staple cartridge (210) also comprises a longitudinally extending vertical slot (222) formed through part of cartridge body (214). Staple cartridge (210) also comprises two rows of staple apertures (216) formed through upper deck (215) on one side of vertical slot (222), and another set of two rows of staple apertures (216) formed through upper deck (215) on the other side of vertical slot (222). Of course, any other suitable number of staple aperture (216) rows may be used. Staple cartridge (210) functions as discussed above with reference to staple cartridge (37). Staples (not shown) are vertically driven out through an associated staple aperture (216) by longitudinal motion of wedge sled (241) within staple cartridge (210). This drives the staples through tissue captured between anvil (268) and upper deck (215), with the forming pockets of anvil (268) forming the staples to secure the tissue.

Cartridge body (214) and lower cartridge tray (212) of staple cartridge (210) each comprise inwardly extending notches (218, 220). Notches (220) of cartridge body (214) are formed at a proximal end (224) of cartridge body (214). Notches (218) of lower cartridge tray (212) are formed at a proximal end (226) of lower cartridge tray (212). Notches (220) of cartridge body (214) and notches (218) of lower cartridge tray (212) are configured to align when cartridge body (214) and lower cartridge tray (212) are coupled together. It should be understood that notches (218, 220) may be located anywhere along cartridge body (214) and/or lower cartridge tray (212), and that the location in the present example is merely one example of one possible location. It should also be understood that notches (218, 220) need not be present in both cartridge body (214) and lower cartridge tray (212). Notches (218, 220) may be incorporated in either cartridge body (214), lower cartridge tray (212), or both cartridge body (214) and lower cartridge tray (212) as in the present example. Finally, it should be understood that any suitable number of notches (218, 220) in cartridge body (214) and/or lower cartridge tray (212) may be used.

Figure 14:
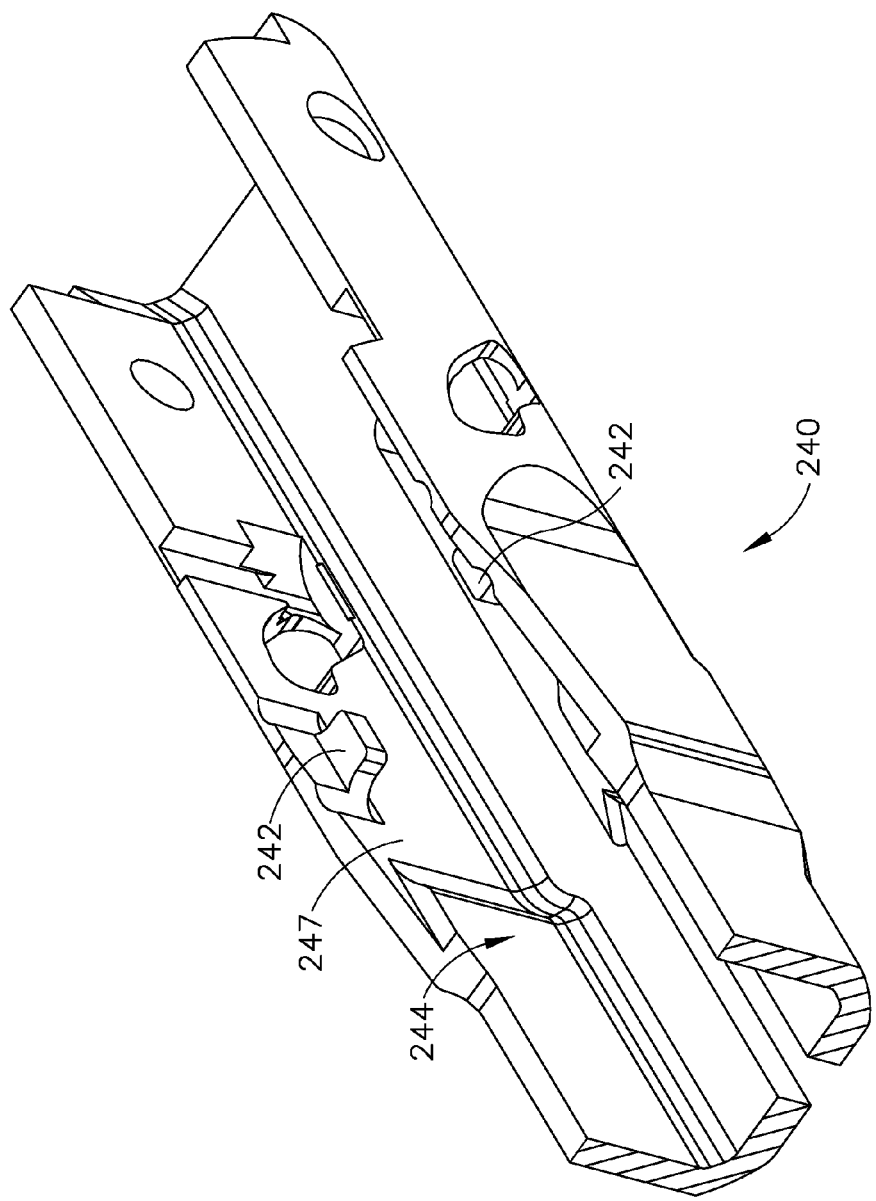
FIG. 14 depicts a detailed perspective view of the proximal portion of an exemplary lower jaw of the end effector of FIG. 12.
Figure 15:
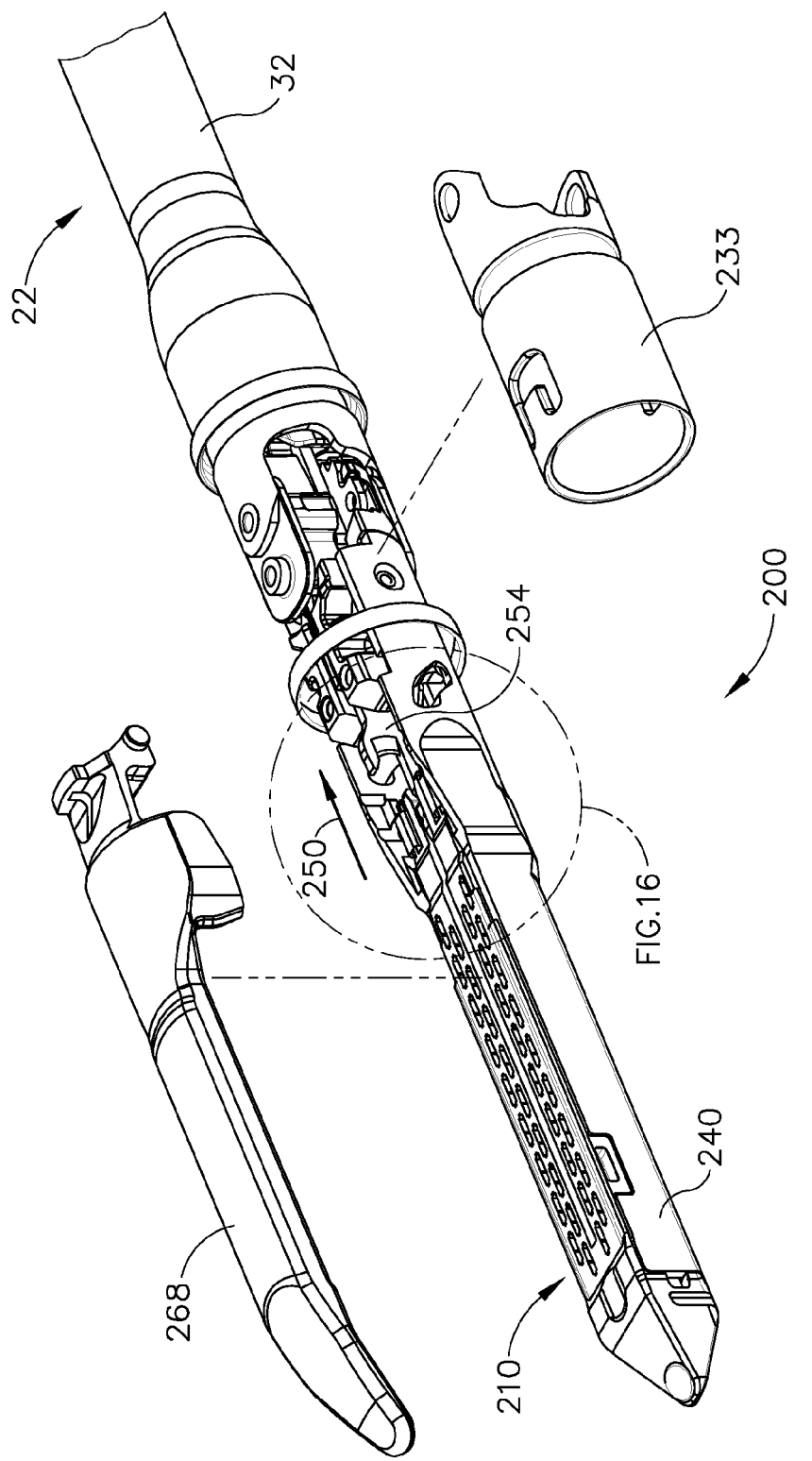
FIG. 15 depicts an exploded perspective view of the end effector of FIG. 12 with the staple cartridge of FIG. 13 and the lower jaw of FIG. 14 assembled.
Figure 16:
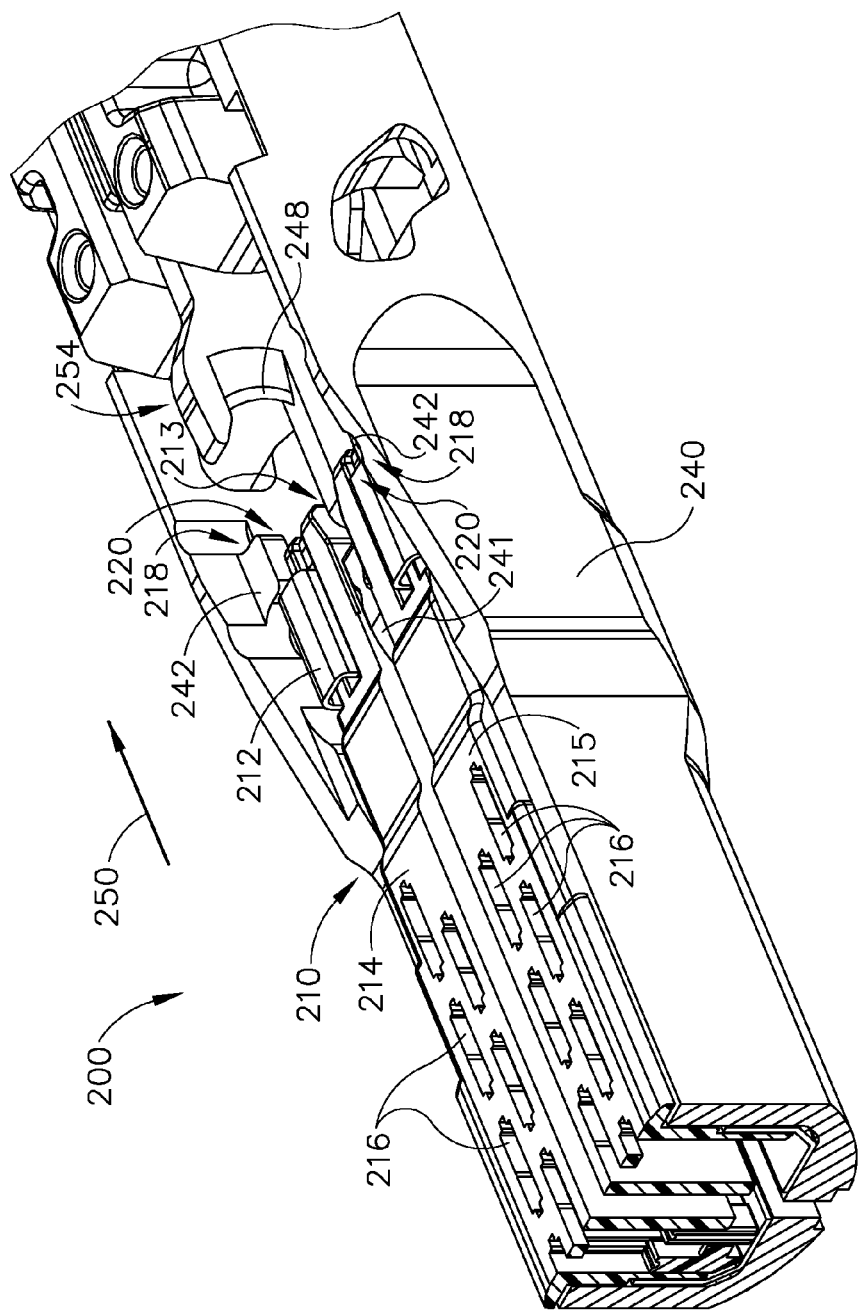
FIG. 16 depicts a detailed perspective view of the end effector of FIG. 12 with the staple cartridge of FIG. 13 and the lower jaw of FIG. 14 assembled.
Figure 17:
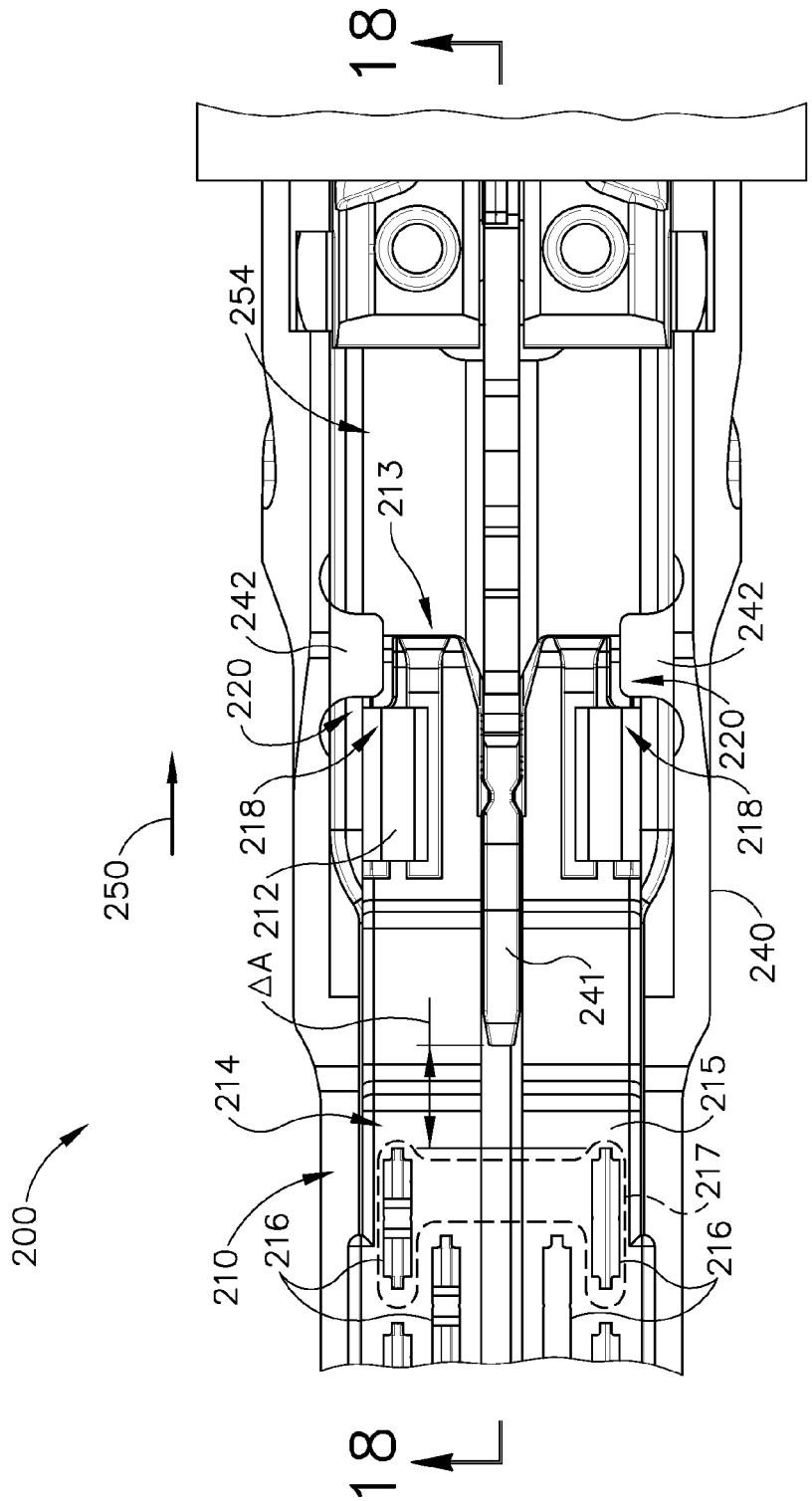
FIG. 17 depicts a detailed top view of the end effector of FIG. 12 with the staple cartridge of FIG. 13 and the lower jaw of FIG. 14 assembled.

As best seen in FIG. 14, lower jaw (240) comprises a channel (244) that is configured to receive staple cartridge (210). Lower jaw (240) is configured to couple with instrument (10) and function as lower jaw (16) in relation to instrument (10) as discussed above. In addition, lower jaw (240) comprises protrusions (242) that protrude inwardly from interior surfaces (247) of lower jaw (240) into channel (244). Protrusions (242) are substantially parallel with a base of lower jaw (240). As shown in FIGS. 15-17, protrusions (242) of lower jaw (240) are configured to mate with notches (220) of cartridge body (214) and notches (218) of lower cartridge tray (212) when staple cartridge (210) and lower jaw (240) are coupled together. It should be understood that protrusions (242) may be located anywhere along lower jaw (240), for instance at a base of lower jaw (240), and that the location in the present example is merely one example of one possible location. It should also be understood that any suitable number of protrusions (242) may be used.

Figure 18:
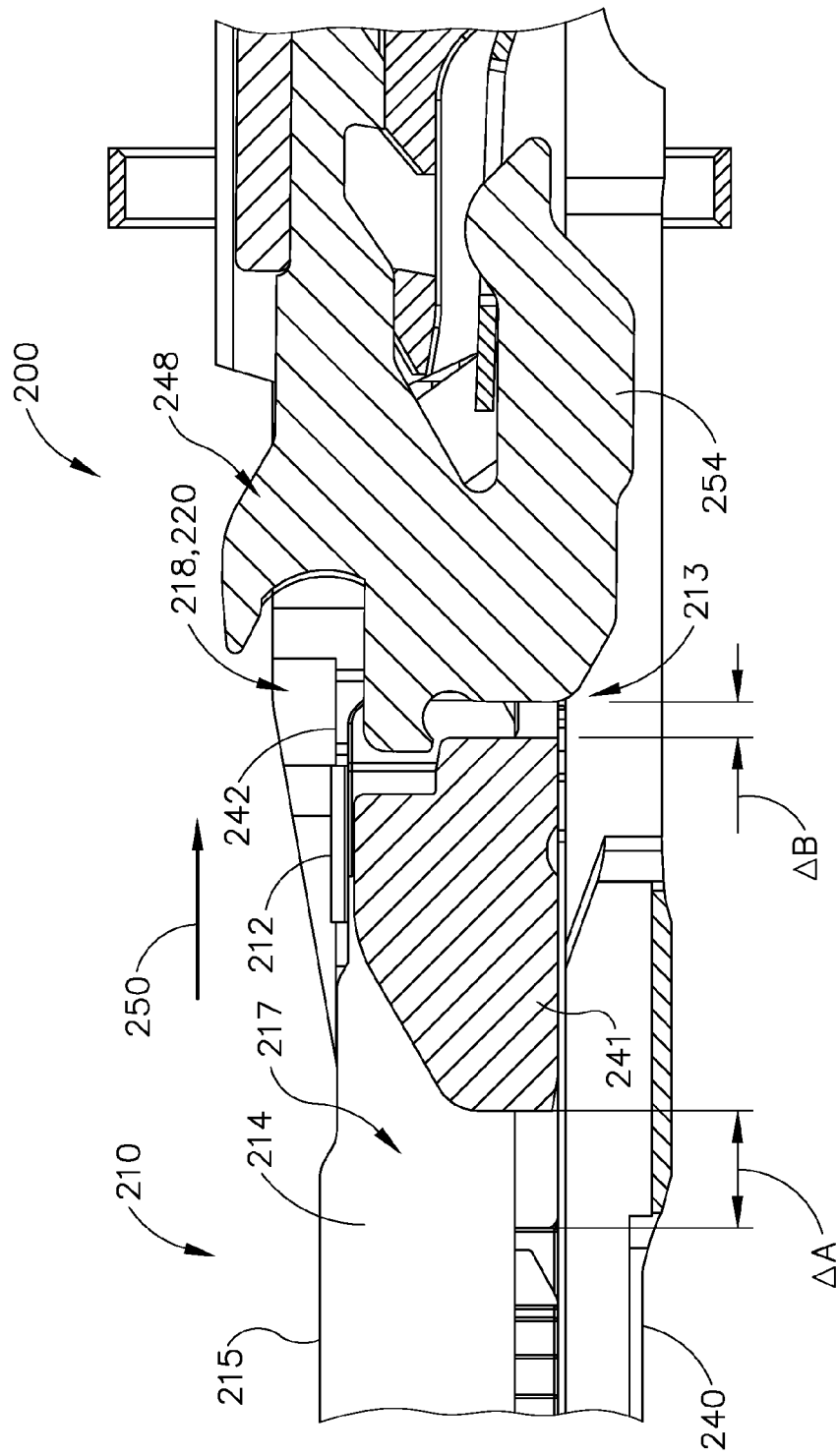
FIG. 18 depicts a detailed cross-sectional view of the end effector of FIG. 12, taken along line 18-18 of FIG. 17, with the staple cartridge of FIG. 13 and the lower jaw of FIG. 14 assembled.

Among other things, protrusions (242) of lower jaw (240) could prevent staple cartridge (210) from sliding proximally beyond protrusions (242) in the direction of arrow (250) as shown in FIGS. 16-18, particularly when staple cartridge (210) is being loaded into lower jaw (240). As shown FIGS. 17 and 18, by preventing staple cartridge (210) from sliding beyond protrusions (242), a gap (ΔA) is consistently maintained between the last row (217) of staple apertures (216) and wedge sled (241). Also, by preventing staple cartridge (210) from sliding beyond protrusions (242), a gap (ΔB) is consistently maintained between wedge sled (241) and firing beam (254). Maintaining gap (ΔB) will maintain gap (ΔA) because maintaining gap (ΔB) ensures that wedge sled (241) remains longitudinally stationary until firing beam (254) is driven distally. Maintaining gaps (ΔA, ΔB) could prevent, among other things, premature distal movement of the wedge sled (241), thereby preventing premature firing of staples and/or premature lockout. This is because, without protrusions (242) and notches (218, 220), staple cartridge (210) may be forced too deeply proximally within channel (244) upon installation or during use. This may cause the stationary firing beam (254) to drive wedge sled (241) distally prematurely, which may cause staples to be vertically driven prematurely. Premature firing of staples and/or other distal movement of wedge sled (241) may cause a lockout condition as discussed above, rendering instrument (10) unusable until the prematurely fired staple cartridge (210) is replaced with an unspent staple cartridge (210). Protrusions (242) of lower jaw (240) may also maintain the position of staple cartridge (210) during operation and prevent staple cartridge (210) from lifting out of lower jaw (240) during tissue compression and/or anvil preload.

Protrusions (242) and notches (218, 220) may cooperate to provide a "poka-yoke" mechanism to help improve product efficiency and/or avoid operator errors or mistakes. This is because, as discussed above, end effector (200) may prevent, among other things, premature distal movement of the wedge sled (241) caused by improper installation of staple cartridge (210), thereby preventing premature firing of staples and/or premature lockout, with little or no effort or consideration by the operator. In addition, protrusions (242) and notches (218, 220) may cooperate to provide a coding/key system to prevent an inappropriately sized/configured staple cartridge (210) from being loaded into lower jaw (240). In other words, different versions of instrument (10) may be configured to operate with only particular kinds of cartridges (210). Each such version of instrument (10) may have protrusions (242) that are uniquely configured to only complement uniquely configured notches (218, 220) formed in the appropriate version of cartridge (210).

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System," published Jan. 10, 2013, now U.S. Pat. No. 8,844,789, issued on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued on Sep. 2, 2014, the disclosure of which is incorporated by reference herein; U.S. Pub. No. 2012/0132450, entitled "Shiftable Drive Interface for Robotically-Controlled Surgical Tool," published May 31, 2012 and issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012 and issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012 and issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued on Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012 and issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, now U.S. Pat. No. 8,573,465, issued on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An end effector, comprising:
   (a) a staple cartridge, wherein the staple cartridge comprises:
      i. a cartridge body, and
      ii. a lower cartridge tray,
      wherein one or both of the cartridge body or the lower cartridge tray comprises at least one proximally presented protrusion engagement feature;
   (b) a jaw, wherein the jaw comprises:
      i. a channel comprising first and second spaced apart interior surfaces and a base extending therebetween, wherein the channel is configured to receive the staple cartridge, and
      ii. at least one protrusion, wherein the at least one protrusion laterally extends from one of the interior surfaces into the channel, wherein the at least one protrusion lies directly over and is spaced apart from the base thereby forming a gap between the at least one protrusion and the base, wherein the gap extends from a bottom surface of the at least one protrusion to a top surface of the base in a direction normal to one or both of the bottom surface of the at least one protrusion or the top surface of the base, wherein the at least one protrusion is positioned to align with the at least one protrusion engagement feature when the staple cartridge and jaw are coupled together, wherein the at least one protrusion and the at least one protrusion engagement feature are configured to restrict movement of the staple cartridge; and
   (c) an anvil, wherein the anvil is coupled to the jaw, wherein the anvil is movable relative to the jaw.

2. The end effector of claim 1, wherein the lower cartridge tray comprises a channel, wherein the channel is configured to receive the cartridge body.

3. The end effector of claim 1, wherein the cartridge body and lower cartridge tray each comprise a proximal end, and wherein the at least one protrusion engagement feature comprises at least one notch formed at the proximal end of one or both of the cartridge body or the lower cartridge tray.

4. The end effector of claim 1, wherein the at least one protrusion engagement feature comprises at least one notch formed in both the cartridge body and the lower cartridge tray.

5. The end effector of claim 4, wherein the same number of notches are formed in both the cartridge body and the lower cartridge tray.

6. The end effector of claim 5, wherein the at least one notch of the cartridge body is positioned to align with the notches of the lower cartridge tray when the cartridge body is received within the channel of the lower cartridge tray.

7. The end effector of claim 6, wherein the jaw comprises the same number of protrusions as the number of notches formed in the lower cartridge tray.

8. The end effector of claim 1, wherein the at least one protrusion comprises at least two protrusions.

9. The end effector of claim 8, wherein each of the at least two protrusions protrudes from a respective one of the interior surfaces.

10. The end effector of claim 1, wherein the at least one protrusion is substantially parallel to the base of the channel of the jaw.

11. The end effector of claim 1, wherein the cartridge body further comprises a plurality of staple apertures.

12. The end effector of claim 1, wherein the anvil comprises a plurality of staple forming pockets.

13. The end effector of claim 1, wherein the end effector further comprises a wedge sled and a firing beam, wherein both the wedge sled and the firing beam are configured to longitudinally slide through the staple cartridge.

14. The end effector of claim 13, wherein the wedge sled is housed within the staple cartridge.

15. The end effector of claim 14, wherein the firing beam includes a distally presented cutting edge.

16. A surgical instrument comprising:
(a) a handle portion;
(b) the end effector of claim 15;
(c) a shaft, wherein the shaft comprises a distal end and wherein the end effector is coupled to the distal end of the shaft;
(d) a first actuator operable to move the anvil toward the jaw; and
(e) a second actuator operable to drive the wedge sled and knife through the staple cartridge.

17. An end effector, comprising:
(a) a staple cartridge, wherein the staple cartridge comprises a cartridge body, wherein the cartridge body comprises a longitudinal slot and a plurality of staple apertures, and wherein the cartridge body comprises at least one notch;
(b) a jaw, wherein the jaw comprises:
i. a channel comprising first and second spaced apart interior surfaces and a base extending therebetween, wherein the channel is configured to receive the staple cartridge, and
ii. at least one protrusion, wherein the at least one protrusion laterally protrudes into the channel from one of the interior surfaces and lies directly over the base forming a gap between the at least one protrusion and the base, wherein the gap is defined between an underside of the at least one protrusion and the base in a direction perpendicular to one or both of the underside of the at least one protrusion or an upper surface of the base, and wherein the at least one protrusion is configured to align with the at least one notch when the staple cartridge and jaw are coupled together, wherein the at least one protrusion is configured to engage the notch to thereby prevent only proximal movement of the cartridge body;
(c) an anvil, wherein the anvil comprises a plurality of staple forming pockets; and
(d) a firing beam, wherein the firing beam is configured to slide through the longitudinal slot.

18. The end effector of claim 17, wherein the staple cartridge further comprises a wedge sled, wherein the firing beam is configured to drive the wedge sled longitudinally through the longitudinal slot, and wherein the wedge sled is configured to vertically drive a plurality of staples through the plurality of staple apertures as it is driven longitudinally through the longitudinal slot.

19. The end effector of claim 17, wherein the firing beam further comprises a knife.

20. A surgical instrument omprising:
(a) a body;
(b) an end effector, wherein the end effector extends distally from the body, and wherein the end effector comprises:
i. a staple cartridge, wherein the staple cartridge comprises a cartridge body having a longitudinal slot, a plurality of staple apertures, and at least one notch and wherein the staple cartridge further comprises a wedge sled configured to drive a plurality of staples through the plurality of staple apertures;
ii. a jaw, wherein the jaw is configured to couple with the staple cartridge, and wherein the jaw comprises at least one inwardly extending protrusion, wherein a gap is formed between the at least one inwardly extending protrusion and the base such that the gap extends from a bottom surface of the at least one inwardly extending protrusion to a top surface of the base in a direction normal to one or both of the bottom surface of the protrusion or the top surface of the base, and wherein the at least one protrusion aligns with and lies directly over the at least one notch when the staple cartridge and jaw are coupled together, wherein the at least one protrusion and at least one notch cooperate to allow the staple cartridge to move in a distal direction but prevent the staple cartridge from moving in a proximal direction;
iii. an anvil, wherein the anvil comprises a plurality of staple forming pockets, wherein the anvil is coupled to the jaw at an axis transverse to a longitudinal axis defined by the jaw, and wherein the anvil is pivotable about the transverse axis; and
iv. a firing beam, wherein the firing beam is configured to slide through the longitudinal slot and wherein the firing beam comprises and a knife;
(c) a shaft, wherein the shaft comprises a distal end, and wherein the end effector is coupled to the distal end of the shaft;
(d) a first actuator operable to pivot the anvil about the transverse axis; and
(e) a second actuator operable to slide the wedge sled and knife through the staple cartridge in response to actuation of the second actuator, wherein the at least one notch and at least one protrusion are configured to cooperate to prevent the wedge sled from contacting the firing beam when the staple cartridge and jaw are coupled together and prior to actuation of the second actuator.

* * * * *